United States Patent [19]

Seki et al.

[11] Patent Number: 4,787,238

[45] Date of Patent: Nov. 29, 1988

[54] METHOD AND DEVICE FOR MEASURING THE QUANTITY OF WATER DAMPENING THE FACE OF AN OFFSET PRINTING PLATE

[75] Inventors: Toshiyuki Seki, Soka; Daiji Suzuki, Urawa, both of Japan

[73] Assignee: Dai Nippon Insatsu Kabushiki Kaisha, Tokyo, Japan

[21] Appl. No.: 5,295

[22] Filed: Jan. 20, 1987

Related U.S. Application Data

[63] Continuation of Ser. No. 783,569, Oct. 3, 1985.

[30] Foreign Application Priority Data

Oct. 8, 1984 [JP] Japan ................... 59-211096
Jun. 11, 1985 [JP] Japan ................... 60-126934

[51] Int. Cl.⁴ ............... G01C 25/00; G01N 21/49; G01N 21/55
[52] U.S. Cl. ................... 73/1 R; 250/341; 356/446; 101/DIG. 24
[58] Field of Search ............... 73/1 R; 356/73, 445, 356/446, 448; 250/341, 358.1; 101/148, DIG. 24; 427/10

[56] References Cited

U.S. PATENT DOCUMENTS

| | | | |
|---|---|---|---|
| 3,994,586 | 11/1976 | Sharkins et al. | 250/341 |
| 4,052,937 | 10/1977 | Lawson et al. | 354/445 |
| 4,129,781 | 12/1978 | Doyle | 250/341 |
| 4,565,450 | 1/1986 | Witz et al. | 356/446 |
| 4,677,298 | 6/1987 | Zelmanovic et al. | 250/341 |

FOREIGN PATENT DOCUMENTS

| | | | |
|---|---|---|---|
| 126613 | 11/1984 | European Pat. Off. | 101/DIG. 24 |
| 58-85135 | 5/1983 | Japan. | |
| 59-55377 | 3/1984 | Japan. | |
| 2150688 | 7/1985 | United Kingdom | 101/148 |

Primary Examiner—Stewart J. Levy
Assistant Examiner—Robert R. Raevis
Attorney, Agent, or Firm—Parkhurst, Oliff & Berridge

[57] ABSTRACT

A method and device for measuring the quantity of water dampening the face of an offset printing plate in which a light beam is made incident at a suitable angle to the face of the printing plate and the light beam directly reflected from the plate at the same angle with the angle of incidence as well as the light beam diffuse-reflected in the direction normal to the face of the printing plate are independently detected so that an image area and a non-image area on the face of the plate are detected in response to the diffuse-reflected light beam; and the variations in level of the directly reflected light beam is calibrated in response to the diffuse-reflected light beam. In order to eliminate the adverse effects caused by the difference in characteristics of light sensors for receiving the directly reflected light beam and the diffuse-reflected light beam, respectively, the outputs of the light sensors for receiving the directly reflected light beam and the diffuse-reflected light beam when the face of the printing plate is sufficiently dampened with water as well as the outputs thereof when the face of the printing plate is completely dried are previously measured so that the calibration of the result of measurement can be calibrated by using the above-described two outputs.

5 Claims, 13 Drawing Sheets

METHOD AND DEVICE FOR MEASURING THE QUANTITY OF WATER DAMPENING THE FACE OF AN OFFSET PRINTING PLATE

This is a continuation of application Ser. No. 783,569 filed Oct. 3, 1985.

BACKGROUND OF THE INVENTION

The present invention relates to a method and display device for measuring and displaying the quantity of water dampening the face of an offset printing plate.

The quantity of water dampening the face of an offset printing plate must be controlled with a high degree of accuracy. So far whether or not the face of an offset printing plate is sufficiently dampened with water is visually detected by an operator who detects the light beam reflected from the layer of water over the face of the plate or who detects visually a printed pattern.

However, when the quantity of water dampening the face of a printing plate is visually observed and controlled by an operator, the results are different from one operator to another. Furthermore, reproducibility is very low. As a result, the quantity of dampening water cannot be controlled.

Therefore there has been a strong demand for a method for measuring the quantity of water dampening the face of an offset printing plate without the visual inspection by an operator and there have been devised and demonstrated various methods utilizing the measurement of the quantity of light beam reflected from the surface of water on the face of the printing plate or the measurement of the quantity of the infrared rays absorbed.

However, when these methods are used in practice, detecting means must be disposed adjacent to the plate cylinder of a press. As a result, the space for installation of such detecting means is limited and the detecting means are contaminated by ink mist. Therefore the above-described methods are not satisfactory in practice in view of environmental conditions, working conditions, sizes, universality and cost.

Especially the environmental conditions have adverse effects. For instance, a light sensor is exposed to normally airborne dust and ink mist scattered from an inking roller so that the output of the light sensor drops to half within about two weeks. Therefore it is important that the device for measuring the quantity of dampening water be able to protect the light sensors from being contaminated and be able to calibrate the gain of the light sensors.

SUMMARY OF THE INVENTION

In view of the above, a first object of the present invention is to provide a method and device capable of correctly measuring the quantity of water dampening the face of a printing plate even under the conditions in which the outputs from light sensors are decreased.

A second object of the present invention is to provide a calibration method for a device for measuring the quantity of dampening water in which even when the optical and electrical characteristics of light sensors vary, the calibration can be made in such a way that the same display can be obtained for the same quantity of dampening water.

In order to attain the first object of the present invention described above, the present invention provides a method and device for measuring the quantity of dampening water in which a light beam is made incident at a predetermined angle to the face of a printing plate and a directly reflected light beam (whose angle of reflection is equal to the angle of incidence) and a diffuse-reflected light beam are detected independently of each other; and the quantity of directly reflected light beam is calibrated with the quantity of diffuse reflected light beam being used as a reference, whereby the quantity of dampening water is detected.

As described above, according to the present invention, a light beam is made incident at a predetermined angle to the face of a printing plate and a directly reflected light beam and a diffuse-reflected light beam are detected independently of each other; and the quantity of directly reflected light beam is calibrated with the quantity of diffuse reflected light beam being used as a reference, whereby the quantity of dampening water can be detected. Therefore, the problem of contamination of light sensors disposed adjacent to a printing press can be substantially overcome so that the quantity of dampening water can be detected with a high degree of accuracy. In addition, the detection of a diffuse-reflected light beam can be also used to detect a non-printing-pattern portion of the printing plate which is applied with dampening water and to detect the clamps for measuring a printing speed. Thus, all the signals required for the calibration of the signal representative of the quantity of dampening water can be obtained by utilizing the output from a light sensor which receives a diffuse-reflected light beam.

As a result, according to the present invention, the quantity of water dampening the face of a printing plate can be measured with a high degree of accuracy so that even an unskilled operator can maintain an optimum quantity of dampening water.

In order to attain the second object of the present invention, the present invention provides a calibration method in which a light beam is made incident at a predetermined angle to the face of a printing plate; the directly reflected light beam whose angle of reflection is equal to the angle of incidence as well as a diffuse-reflected light beam are detected independently by respective light sensors; the output of the directly reflected light beam when a non-image area portion on the face of the plate is supplied with a sufficient quantity of dampening water and the output of the directly reflected light beam when the dampening water is gradually evaporated and the face of the plate is completely dried, are automatically detected and stored so that the calibration of the detected quantity of dampening water can be made by utilizing the above described outputs from the light sensor.

As described above, according to the present invention, the quantity of the directly reflected light beam is calibrated in response to the initial value obtained when a sensor is first installed, whereby the quantity of dampening water can be measured. Therefore the problems that light sensors disposed adjacent to a press are contaminated, the sensors are erratically installed, and the output of the sensor is offset when the face of the plate is completely dried, can be substantially overcome so that the correct measurement is possible.

DESCRIPTION OF THE PREFERRED EMBODIMENT

Figure 1:
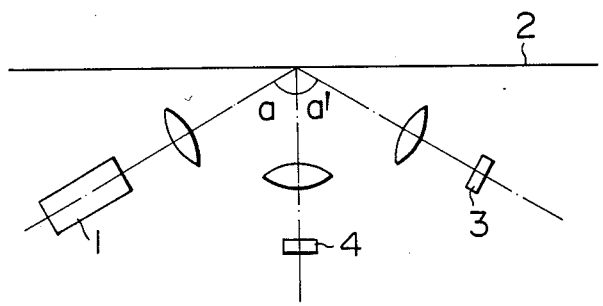
FIG. 1 is a schematic view used to explain the underlying principle of the present invention.

FIG. 1 shows the underlying principle of the present invention for detecting the quantity of water dampening the face of a plate. The light emitted from a light source 1 impinges the face of a plate 2 at an angle a and the light which is reflected by an angle a' which is equal to the angle of incidence a is detected by a first light sensor 3 while the light which is diffuse reflected normal to the face of the plate 2 is detected by a second light sensor 4.

The angle of incidence a (the angle of reflection a') can be arbitrarily selected and it is confirmed that if practical problems are neglected, Fresnel equations and experimental results show that the greater the angle of incidence a (=the angle of reflection a'), the greater the quantity of reflected light becomes and therefore the higher the detection sensitivity becomes. The wavelength of the light emitted from the light source 1 may be also arbitrarily selected.

Figure 2:
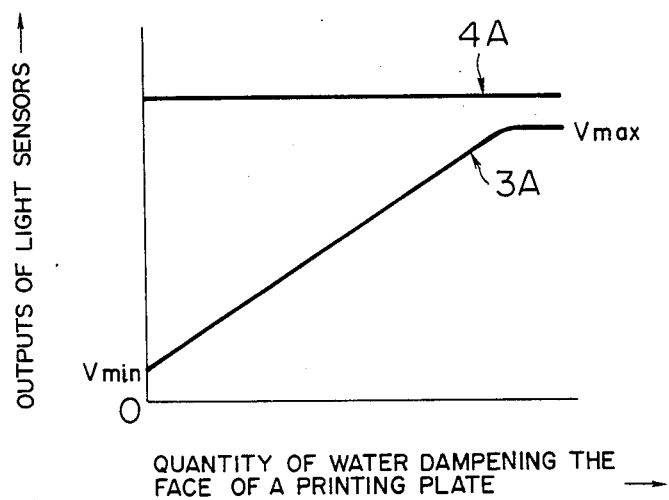
FIG. 2 shows the relationship between the quantity of water dampening the face of a printing plate and the output from light sensors arranged as shown in FIG. 1.

FIG. 2 shows the output characteristic curves of the first light sensor 3 and the second light sensor 4 which are disposed as shown in FIG. 1. The quantity of water dampening the face of the plate is plotted along the abscissa while the outputs from the light sensors 3 and 4 along the ordinate. The output characteristic curve of the first sensor 3 is indicated by 3A and it is readily seen that the output of the first light sensor 3 is in proportion to the quantity of water dampening the face of the plate, but the output characteristic curve 4A of the second light sensor 4 remains constant regardless of the quantity of water dampening the face of the plate. FIG. 2 shows only the relationship between the quantity of water dampening the face of the plate and the outputs from the first and second light sensors, but it is understood that when the light rays reflected from the face of the plate 2 vary, the outputs of the first and second light sensors 3 and 4 also vary. The outputs from the first and second light sensors 3 and 4 vary because of external disturbances such as ink mist, dust contamination, aging of the light source, the deviation of the light sensors and so on. Both the first and second light sensors 3 and 4 experience the same variation.

It follows therefore that if the output of the first light sensor 3 is corrected in response to the output from the second light sensor, the quantity of water dampening the face of the plate 2 can be correctly measured.

It is assumed that the output of the first light sensor 3 is A while the output of the second light sensor 4 is B when there exists no external disturbance and that the output variations become $\alpha$ and $\beta$, respectively, when external disturbances exist. Then when there exist external disturbances, the outputs become $\alpha A$ and $\beta B$, respectively. It is further assumed that if there exist external disturbances, both the first and second light sensors are affected by the same degree; that is, $\alpha = \beta$. Then the ratio between the outputs becomes $$\frac{\alpha A}{\beta B} = \frac{\alpha A}{\alpha B} = \frac{A}{B}$$

It is seen that the effects due to the external disturbances are cancelled. When the first and second light sensors are differently affected due to the external disturbances; that is, when $\alpha \neq \beta$, the relation between $\alpha$ and $\beta$; that is, $\alpha = f(\beta)$ is previously obtained. As the result, the output ratio becomes $$\frac{\alpha A}{f(\beta)B} = \frac{\alpha A}{\alpha B} = \frac{A}{B}$$

It is also possible therefore to cancel the effects of external disturbances. It follows therefore that when the output from the first and second light sensors are computed, the quantity of water dampening the face of the plate can be measured independently of external disturbances.

In this embodiment, the quantity of water dampening the face of plate is denoted by 0% when the face of the plate is completely dry and the quantity of water dampening the face of the plate in excess of a required quantity (saturation) is denoted by 100%. Thus in this embodiment, the quantity of water dampening the face of the plate is expressed by a relative value. The reference conditions are denoted by $V_{min}$ and $V_{max}$ in FIG. 2.

Even when the face of the plate is completely dry, some reflected light rays are intercepted by the first and second light sensors so that their output do not become zero. Therefore the quantity of water dampening the face of the plate is given by the following equation.

$$\frac{Ve - V_{min}}{V_{max} - V_{min}}$$

where Ve is a value obtained by the above-described correction method, Vmin is the value obtained when the quantity of water damping the face of the page is 0%, and Vmax is the value obtained when the quantity of water damping the face is 100%.

Figure 3A:
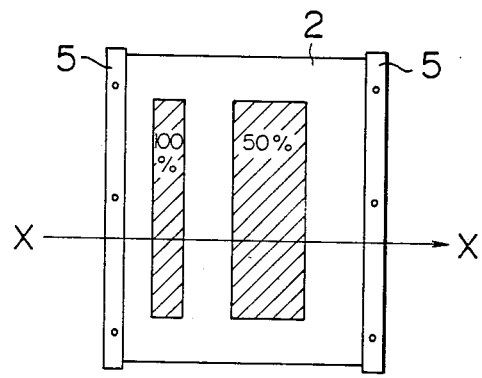
FIGS. 3(a), (b) and (c) show the output of the light sensors when they scan the face of a plate.
Figure 3B:
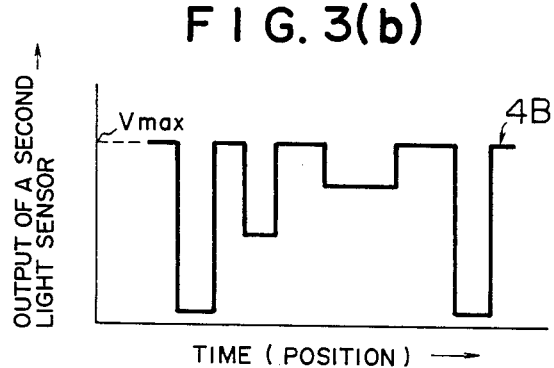
Figure 3C:
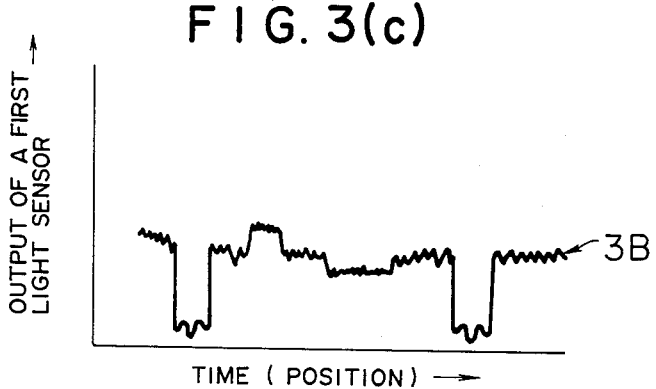

FIGS. 3(a), (b) and (c) show a scanning method and the outputs from the first and second light sensors when the face of a plate is dampened with water in order to detect non-image area portions. As shown in FIG. 3(a), the plate 2 is provided with a region with 100% pattern area rate and a region with 50% pattern area rate. The plate 2 is scanned from one clamp 5 to another clamp 5 in the direction indicated by X—X so as to traverse the two regions. In this case, the output waveform of the second light sensor which receives the diffuse reflected light rays is shown in FIG. 3(b) while the output waveform of the first light sensor which receives the directly reflected light rays is shown in FIG. 3(c). The output 4B of the second light sensor which is shown in FIG. 3(b) is not affected by the water on the face of the plate and drops in response to the area of a pattern. Therefore the output is always the maximum output $V_{max}$ when there is no image area.

Therefore the maximum output $V_{max}$ of the second light sensor is so set as to be within a predetermined allowable range for one rotation of a plate cylinder. When the output from the second light sensor is within this allowable range, the non-image area is determined as being detected. And when the output or water-quantity signal 3B from the first light sensor is detected and sampled only at the position corresponding to the non-image area, the signal representative of the quantity of water on the non-image area can be obtained.

The measurement of the printing speed which is required to determine a sampling interval is computed by utilizing the output of the second light sensor when the latter scans the clamps.

Figure 4:
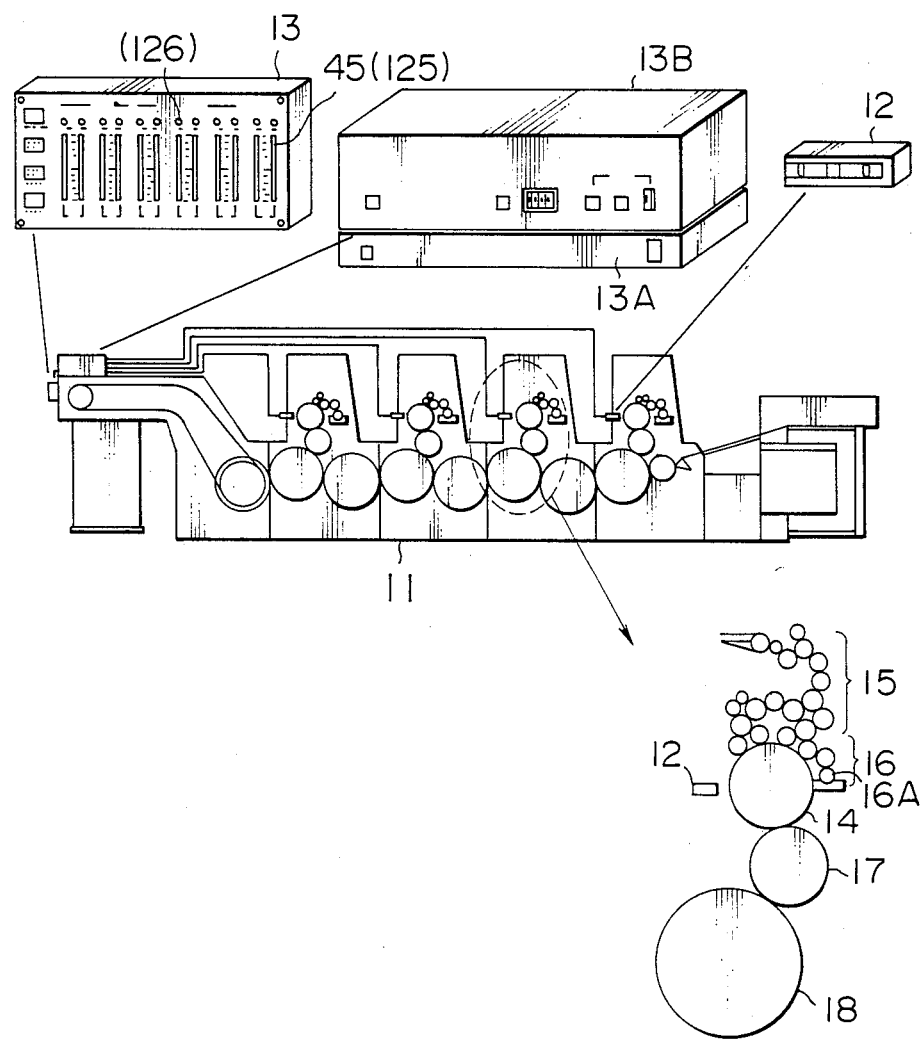
FIG. 4 shows the outer appearance of an offset sheet-fed press incorporating a device in accordance with the present invention.

FIG. 4 is a schematic view of an offset sheet-fed press incorporating the devices for measuring the quantity of water dampening the face of the plate in accordance with the present invention. The device in accordance with the present invention has a sensor 12, a display device 13, a control unit 13A and an operational unit 13B which are disposed at predetermined positions in a printing press 11. More specifically, the sensor 12 is disposed adjacent to the plate cylinder 14 in each unit of the printing press. The plate cylinder 14 is not only supplied with ink from an inking roller 15 but also supplied with dampening water from a dampening arrangement 16. The plate cylinder 14 coacts with a blanket roller 17 and a pressure roller 18 to print. The signal detected by the sensor 12 is applied to the operational unit 13B so as to calculate the quantity of water on the non-image area, which is displayed at a LED display 45 on the panel of the display device 13 as well as applied to the control unit 13A so as to control the rotational speed of the water fountain roller 16A to maintain the desired quantity of water.

A non-image area can be also detected in the manner described hereinafter. A rotary encoder is incorporated into a system for driving a plate cylinder and the non-image area can be detected by comparing the data previously input by an operator with the output from the rotary encoder.

Figure 5:
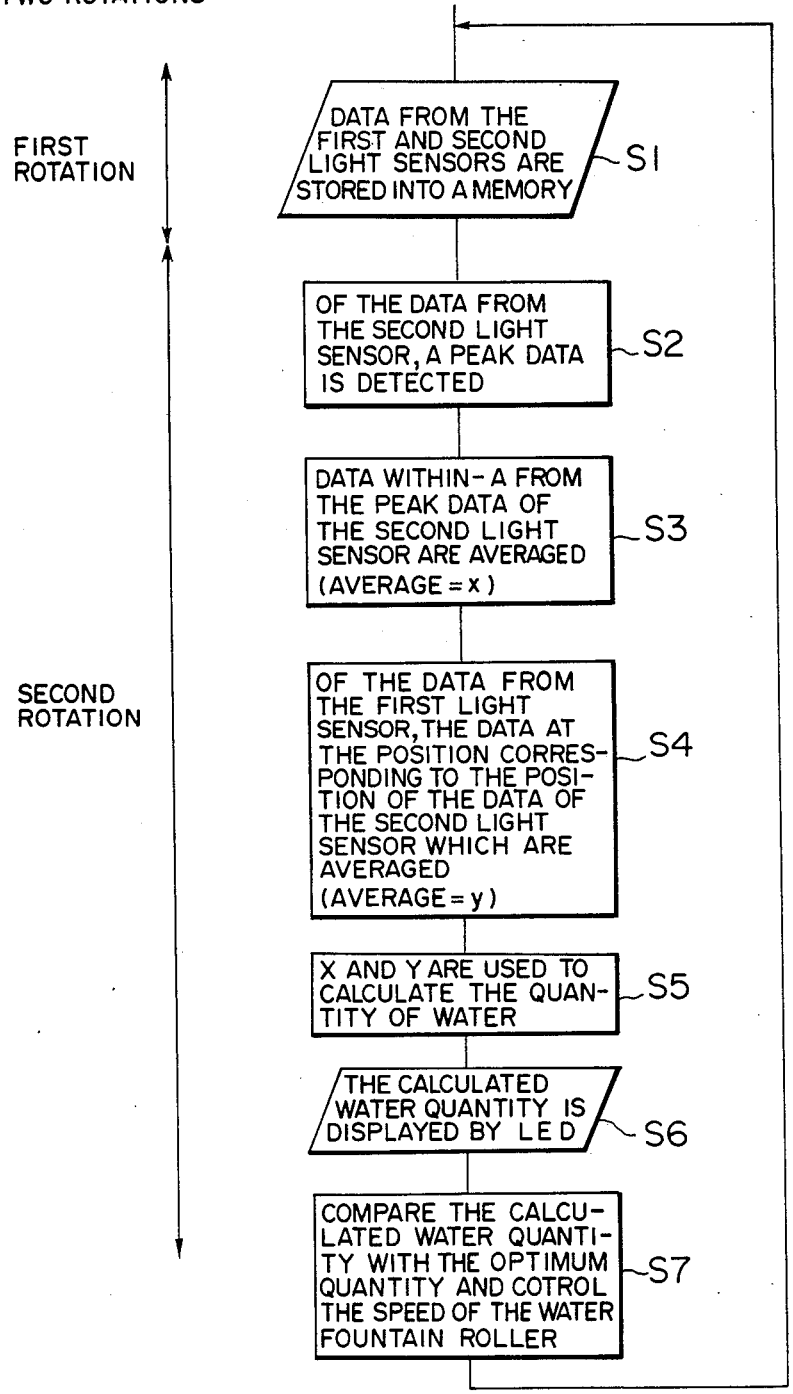
FIG. 5 is a flowchart of a program carried out by an operational unit shown in FIG. 4.

FIG. 5 is a flowchart of a program carried out by the operational unit 13B shown in FIG. 4. Upon the completion of one rotation of the plate cylinder, the light quantity data obtained from the first and second light sensors in the sensor 12 are delivered for each of predetermined interval on the face of the plate to a memory (S1). Upon the completion of the second rotation of the plate cylinder, of the data stored in the memory, the data from the second light sensor which is not affected by the quantity of water is read out so as to detect the peak data (S2). The values within the width of -a from the peak value are averaged (S3) and is set as x. Thereafter of the data of the first light sensor which varies in response to the quantity of water, the data for the same position as the data for determining the value x is derived is read out and the average value y is determined (S4). The quantity of water is calculated in response to the values x and y (S5) and the result is applied to the display device 13 and is displayed by a light-emitting diode display 45 (S6). The measured quantity of water is compared with an optimum quantity stored in the memory in the operational unit 13B and if required the instruction is given to the control unit 13A so that the rotational speed of the water fountain roller 16A is increased or decreased (S7). In response to the instruction from the operational unit 13B, the control unit 13A increases or decreases the rotational speed of the water fountain roller 16A (S7). The above-described sequence is repeated so that the light-emitting diodes LED display the quantity of water for each rotation and the optimum quantity of dampening water can be maintained.

Figure 6:
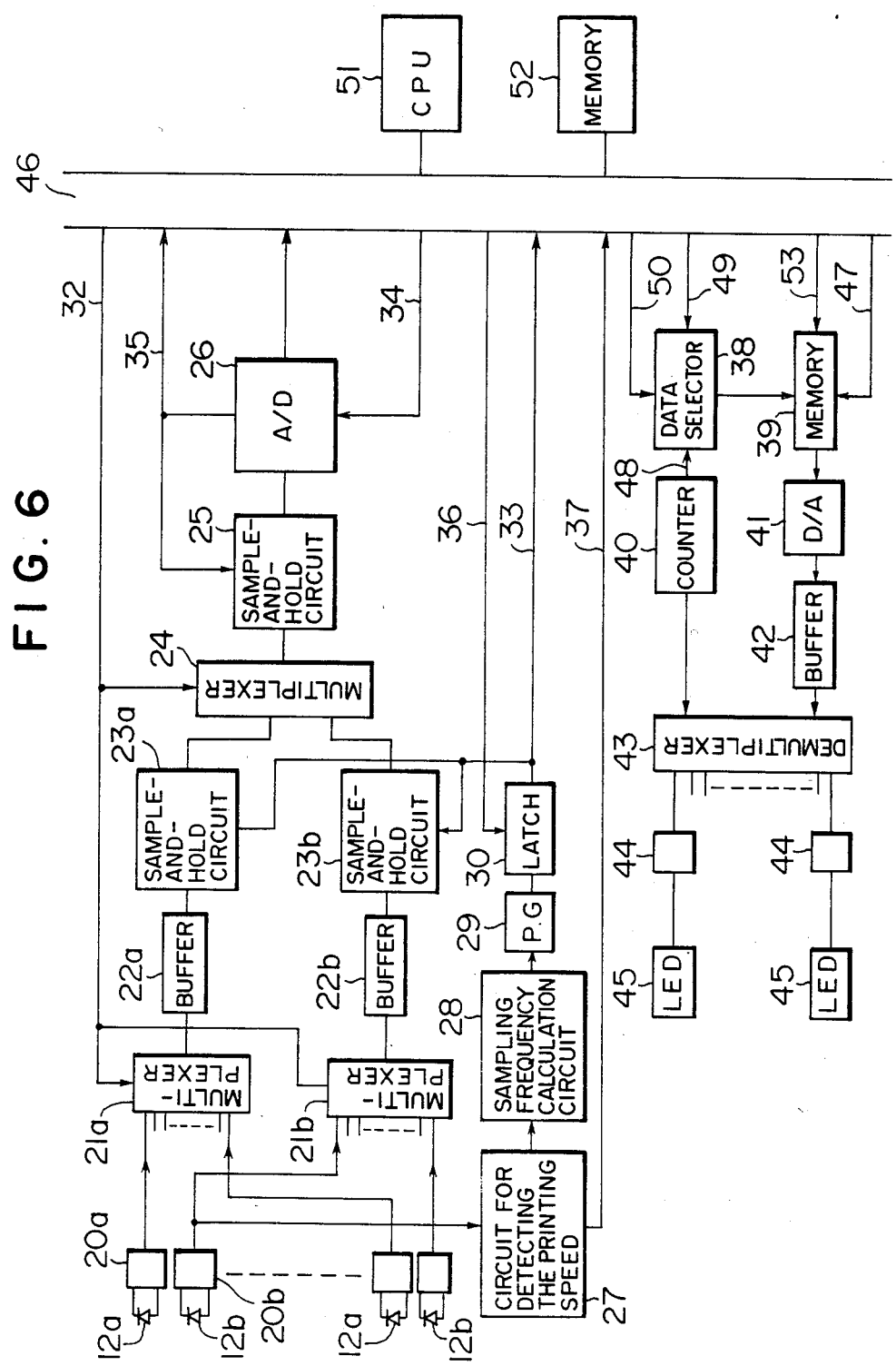
FIG. 6 is a block diagram of an electronic circuit of the operational unit.

FIG. 6 is a block diagram of an electronic circuit for carrying out the above-described steps.

The area on the face of the plate where the quantity of dampening water is to be measured is not limited to one area and a plurality of areas in the widthwise direction of the plate cylinder must be measured. In addition, one sensor must be provided for each of color units in the case of a multicolor press. Therefore, a plurality of sensors 12 can be connected in this electronic circuit.

A sensor 12 comprises a first light sensor 12a for measuring the quantity of water and a second light sensor for correcting the output and detecting the position of a non-image area. The outputs from the first and second light sensors 12a and 12b are delivered through photocurrent-voltage converters 20a and 20b to multiplexers 21a and 21b, respectively. In response to a channel selection signal delivered from CPU 51, one of the input lines of each of the multiplexers 21a and 21b is selected and the output from the multiplexers 21a and 21b are applied through buffer amplifiers 22a and 22b to sample-and-hold circuits 23a and 23b.

The output of the second light sensor 12b is applied to a circuit 27 for measuring a printing speed and in response to a clamp signal, the printing speed is measured. The output from the circuit 27 is applied to a sampling frequency computation circuit 28 so that a sampling frequency at which a predetermined spacing can be sampled independently of the printing speed is computed. The output of the circuit 28 is applied to a pulse generator 29 so that sampling pulses as the above-described sampling frequency are generated. The sampling pulses are applied through a latch 30 to the sample-and-hold circuits 23a and 23b so that the signals from the first and second light sensors 12a and 12b are simultaneously held. The held signals are sequentially switched by a multiplexer 24 and are applied through a sample-and-hold circuit 25 to an A/D converter 26 output of which is stored as digital signals in a memory 52.

Figure 7:
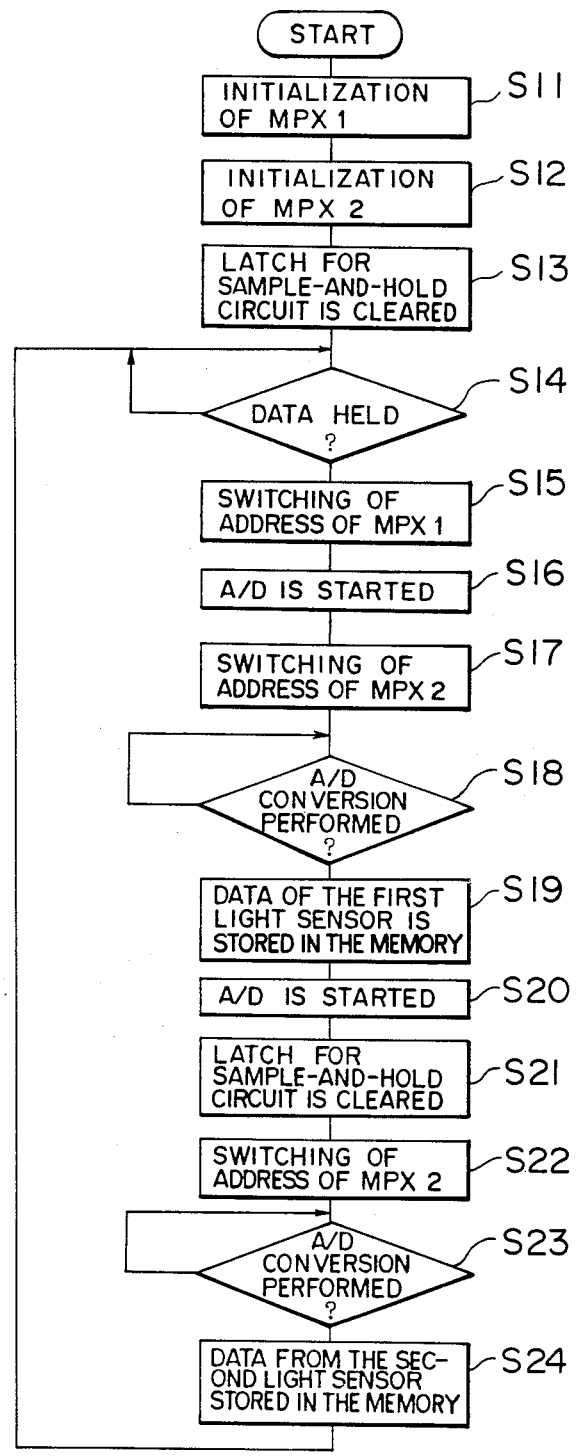
FIG. 7 is a flowchart showing the operations carried by the electronic circuit shown in FIG. 6.

CPU 51 controls the A/D conversion according to the flowchart as shown in FIG. 7. Referring now to FIG. 7, CPU first effects the initialization (S11, S12) of 24 channels of the multiplexers 21a and 21b and clears (S13) the sample-and-hold latch 30 and is watching the output line thereof. When data is held (S14), the channels of the multiplexers 21a and 21b are switched to the next channels (S15). In this case, the multiplexer 24 selects the output from the first light sensor and CPU 51 delivers a conversion start signal 34 to the A/D converter 26. Thereafter CPU 51 switches the channel of the multiplexer 24 to the signal from the second light sensor (S17) and after the conversion, is watching the conversion-completion signal 35. After the A/D conversion (S18), the data from the first light sensor is stored in the memory 52 (S19). At this time point, the signal from the second light sensor is already applied to the input of the A/D converter so that the A/D-conversion-start signal 34 is immediately delivered (S20). Thereafter CPU 51 delivers a clear signal 36 to the sample-and-hold latch 30 (S21) so that the multiplexer 24 is switched to the signal from the first light sensor (S22) and CPU 51 monitors the conversion-completion signal 35. After the A/D conversion (S23), the data from the second light sensor is stored in the memory 52 (S24). CPU 51 sequentially repeats the above-described steps and the clamp signal 37 is delivered from the circuit 27. When the data of one rotation is stored, CPU 51 is interrupted in response to the clamp signal 37 so that the computation for measuring the quantity of dampening water is started.

The quantity of water computed by CPU 51 is converted from the digital signal to the analog signal, which is applied to LEDs. In this embodiment, as shown in FIG. 6, the so-called dynamic lighting system is employed so that a plurality of LED units can be displayed by one D/A converter. More specifically, the data of the quantity of water is stored in a display memory 39 and is sequentially read out in response to the memory address; that is, the content of a counter 40 which is running at a high speed. The output from the memory 39 is applied to a D/A converter 41 and the output from the D/A converter 41 is applied through a buffer 42 and a demultiplexer 43 to the LED 45. The channel signal of the demultiplexer uses the same value as the above-described memory address and is in synchronism with the readout of memory data.

In order to refresh the data in the display memory 39, among address lines 48 and 49 the line 49 is selected in response to the selector signal input 50 of an address selector and a write signal 47 and a new data 53 are applied to the display memory 39. The dynamic lighting of LEDs is accomplished by the above described method.

One example of the sequence of the control of the rotational speed of the water fountain roller is as follows. An operator watches the quantity of water displayed by the rod-shaped LED of the display device or a printed pattern. When the operator detects an optimum quantity of water, he or she depresses an optimum-water-quantity input switch on the display device and then controls the rotational speed of the water fountain roller in such a way that the face of the printing plate is applied with an optimum quantity of dampening water as will be described in more detail hereinafter.

Figure 13:
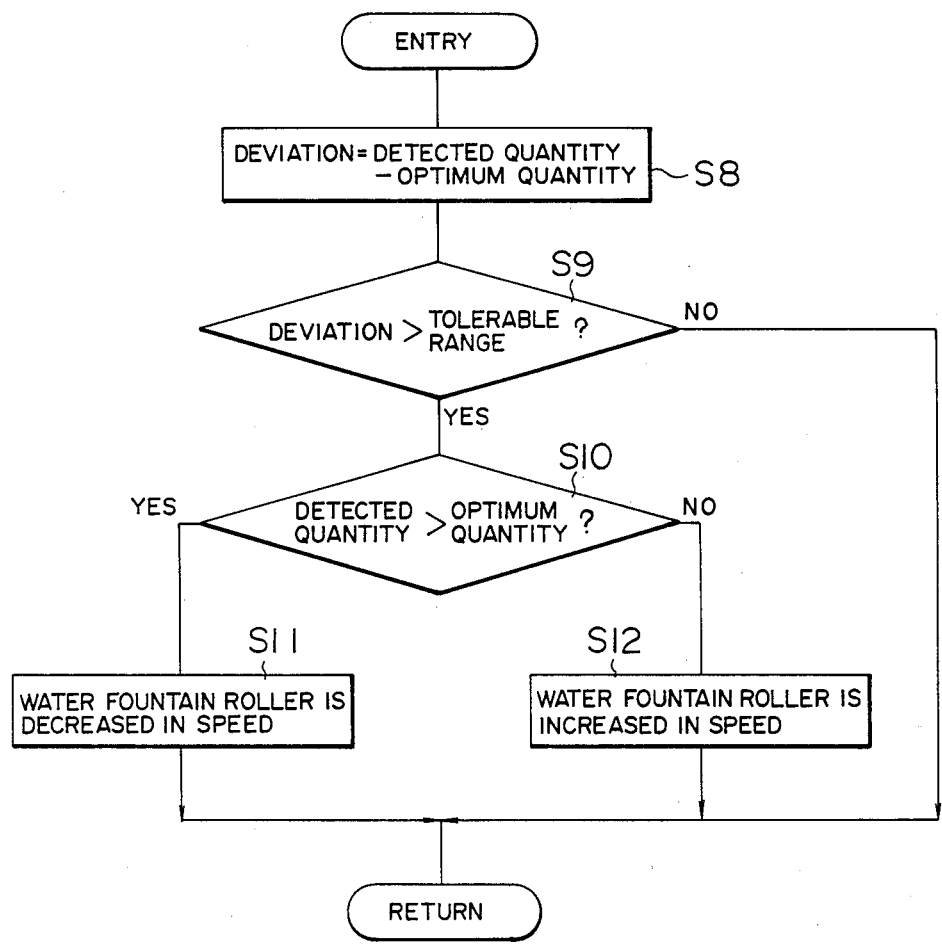
FIG. 13 is a flowchart used to explain in more detail the flowchart shown in FIG. 5.

FIG. 13 shows the more detailed sequence of the step S7 shown in the flowchart of FIG. 5.

First the difference between the computed or measured quantity of dampening water and an optimum quantity of dampening water stored in the memory 24 when the optimum-water-quantity input switch is depressed is obtained (S8). Thereafter the difference thus obtained is compared with a predetermined tolerable or allowable range which is set by a digital switch or the like (S9). When the difference or deviation is lower than the tolerable range, next step is performed without increasing or decreasing the rotational speed of the water fountain roller. When the difference or deviation is in excess of the tolerable range, whether the measured quantity is greater than or smaller than the optimum quantity is detected (S10). When the measured quantity is greater, the water fountain roller is decreased in rotational speed (S11), but when the measured quantity is smaller, the water fountain roller is increased in speed (S12).

It is to be understood that the degree of acceleration or deceleration of the water fountain roller may be maintained constant regardless of the degree of difference or deviation. Alternatively, the so-called proportional control may be employed so that the acceleration or deceleration is in proportion to the difference or deviation.

So far the measurement of the quantity of water dampening the face of the plate, the display of the quantity of water and the automatic control of the rotational speed of the water fountain roller have been described, but it is understood that the numerical values of the nip pressure and the skew adjustment which play a very important role in adjusting the quantity of dampening water can be also obtained. To this end, a water quantity sensor is designed and constructed so as to be movable. Alternatively, a plurality of sensors are disposed in the widthwise direction of the plate cylinder and their outputs are utilized.

The display device may be provided with a pointer which can be arbitrarily set by an operator in order to adjust the quantity of dampening water. Furthermore, it may be provided with an alarm device which produces an alarm signal when the quantity of dampening water is in excess of a predetermined level. Moreover, the device of the present invention is used to automatically control the nip pressure and the skew.

Figure 8:
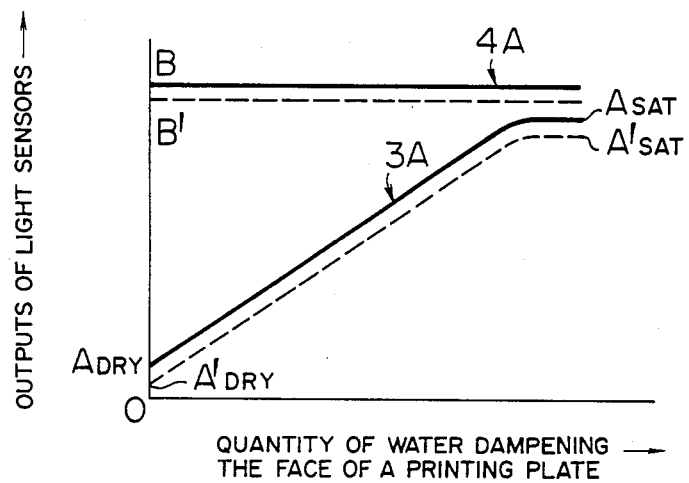
FIG. 8 shows the detection characteristics of the light sensors shown in FIG. 1.

FIGS. 8-12 are views used to explain the calibration of the device of the type described above. FIG. 8 shows the output characteristics of the first and second light sensors 3 and 4 which are arranged as shown in FIG. 1. The quantity of water dampening the face of the plate is plotted along the abscissa while the outputs from the light sensors along the ordinate. The output curve 3A of the first light sensor 3 varies in proportion to the quantity of water dampening the face of the plate while the output curve 4A of the second light sensor 4 remains constant almost independently of the quantity of water dampening the face of the plate. FIG. 8 shows only the relationship between the quantity of water dampening the face of the plate and the outputs from the first and second sensors, but it is to be understood that the outputs from the first and second light sensors vary in response to the variation of light rays reflected from the face of the plate 2.

Next the correction of optical and electrical variations of a plurality of sensors and the correction of the zero point between the outputs from the light sensors and the quantity of water dampening the face of the plate are described. In this embodiment, the quantity of water dampening the face of the plate is denoted by 0% when the face of the plate is completely dried and the quantity of water dampening the face of plate in excess of a predetermined level (saturation) is represented by 100%. The reference conditions are represented by $A_{DRY}$ and $A_{SAT}$, respectively, in FIG. 8.

In the device in accordance with the present invention, some light rays are reflected from the face of the plate even when the plate is dried so that the outputs from the light sensors will not become zero. Therefore the quantity of dampening water is given by Eq. (1)

$$\frac{A - A_{DRY}}{A_{SAT} - A_{DRY}} \quad (1)$$

where A is the output from the first light sensor;
$A_{DRY}$ is the output from the first light sensor; when the plate is dry; and
$A_{SAT}$ is the output from the first light sensor when the face of the plate is saturated with dampening water. Therefore the correction of variations of a plurality of sensors and the correction of the zero point can be effected by Eq. (1).

Meanwhile, the output levels of the first and second light sensors vary because the light receiving surfaces of the sensors are contaiminated by external disturbances such as ink mist, dust and the like. In this case, the variation in level can be corrected in response to the output of the second light sensor which does not vary in response to the variation in quantity of dampening water as will be described below.

It is assumed that the output of the first light sensor when the face of the plate is saturated with the dampening water or when the light sensor is adversely affected by the external disturbances be $A_{SAT}$ and that the outputs of the first and second light sensors when the plate is dry are $A_{DRY}$ and B, respectively.

When the external disturbances occur as described above, the outputs drop as indicated by the broken line curves as shown in FIG. 8 so that the outputs from the first and second sensors become $A'_{SAT}$, $A'_{DRY}$ and $B'$. It is assumed that the output variation rates of the first and second light sensors are $\alpha$ and $\beta$ when they are adversely affected by the external disturbances. Then $$A'_{SAT} = \alpha A_{SAT} \quad (2)$$

$$A'_{DRY} = \alpha A_{DRY}$$

$$A' = \alpha A$$

$$B' = \beta B;$$

where $\alpha \neq \beta$. According to the experimental results, the relation between $\alpha$ and $\beta$ is expressed by $$\alpha = \beta^b \quad (3)$$

where b is a constant between 1.0 and 2.0. Therefore the quantity of water dampening the face of the plate is given by $$\frac{A - A_{DRY}}{A_{SAT} - A_{DRY}} = \frac{\frac{A'}{\alpha} - A_{DRY}}{A_{SAT} - A_{DRY}} = \quad (4)$$

$$\frac{A' - \alpha A_{DRY}}{\alpha A_{SAT} - \alpha A_{DRY}} = \frac{A' - \beta^b A_{DRY}}{\beta^b A_{SAT} - \beta^b A_{DRY}} =$$

$$\frac{A' - \left(\frac{B'}{B}\right)^b A_{DRY}}{\left(\frac{B'}{B}\right)^b A_{SAT} - \left(\frac{B'}{B}\right)^b A_{DRY}}.$$

where: $\alpha$ is the output variation rate of the first sensor; $\beta$ is the output variation rate of the second sensor and is expressed $b\sqrt{\alpha}$; and b is a constant having a value between 1.0 and 2.0.

Thus the level can be corrected by the decrease rate $\beta$ of the output B of the second light sensor. A is the output from the first light sensor when the quantity of dampening water is measured and B is the output from the second light sensor at its initial status and is stored in the memory as a constant when the operation for inputing the initial value is rendered.

Figure 9:
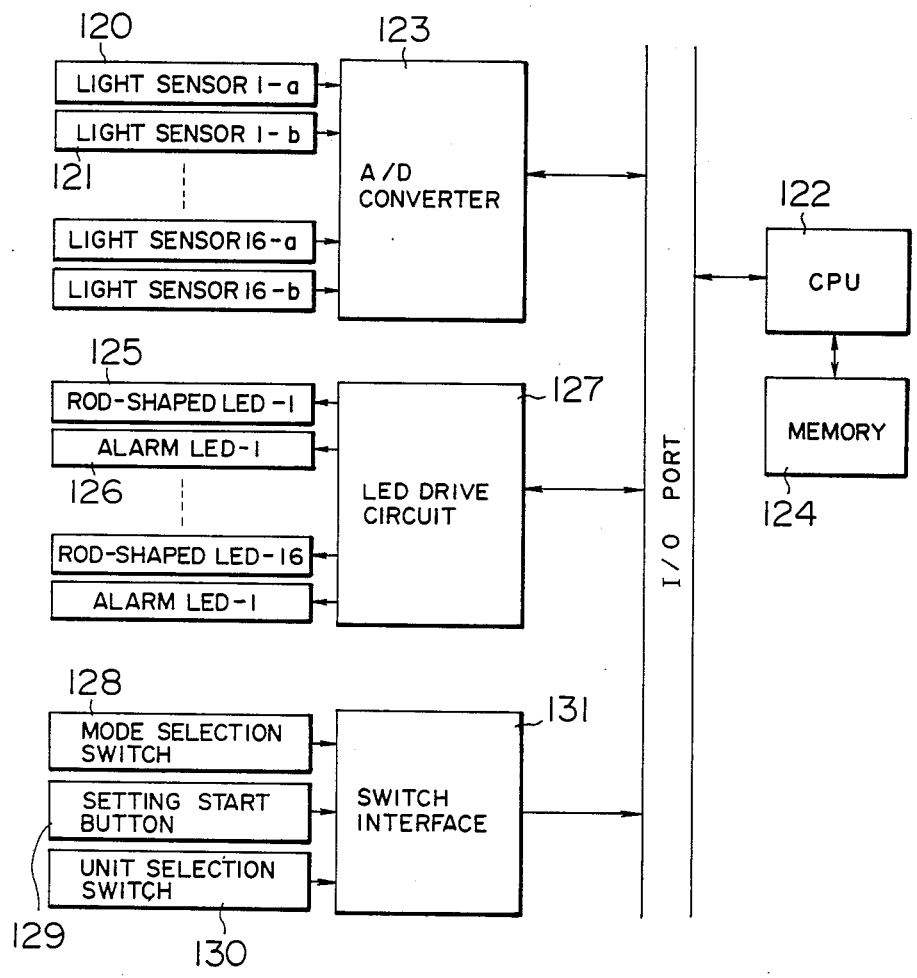
FIG. 9 is a block diagram of a device for accomplishing the calibration of a device for measuring the quantity of dampening water in accordance with the present invention.

FIG. 9 is a block diagram of a device for measuring the quantity of dampening water in accordance with the present invention.

The outputs from light sensors 1-a, 2-a, ... and 16-a which receive the directly reflected light rays and the outputs from light sensors 1-b, 2-b, ... and 16-b which receive the diffuse reflected light rays are converted in an A/D converter 123 from the analog signals to the digital signals in response to a control signal from CPU 122 and the digital signals are stored in a memory 124. A set of LEDs comprises a rod-shaped LED 125 which displays the quantity of dampening water and a LED 126 which produces a signal representative of the contamination of the sensor. Displays are made in response to display data delivered from CPU 122 to a LED drive circuit 127. While the automatic recognition of the initial value is being made, the rod-shaped LED 125 displays the output itself of the first light sensor and the alarming LED 126 is used as a means for indicating that the automatic recognition is being made.

Figure 10:
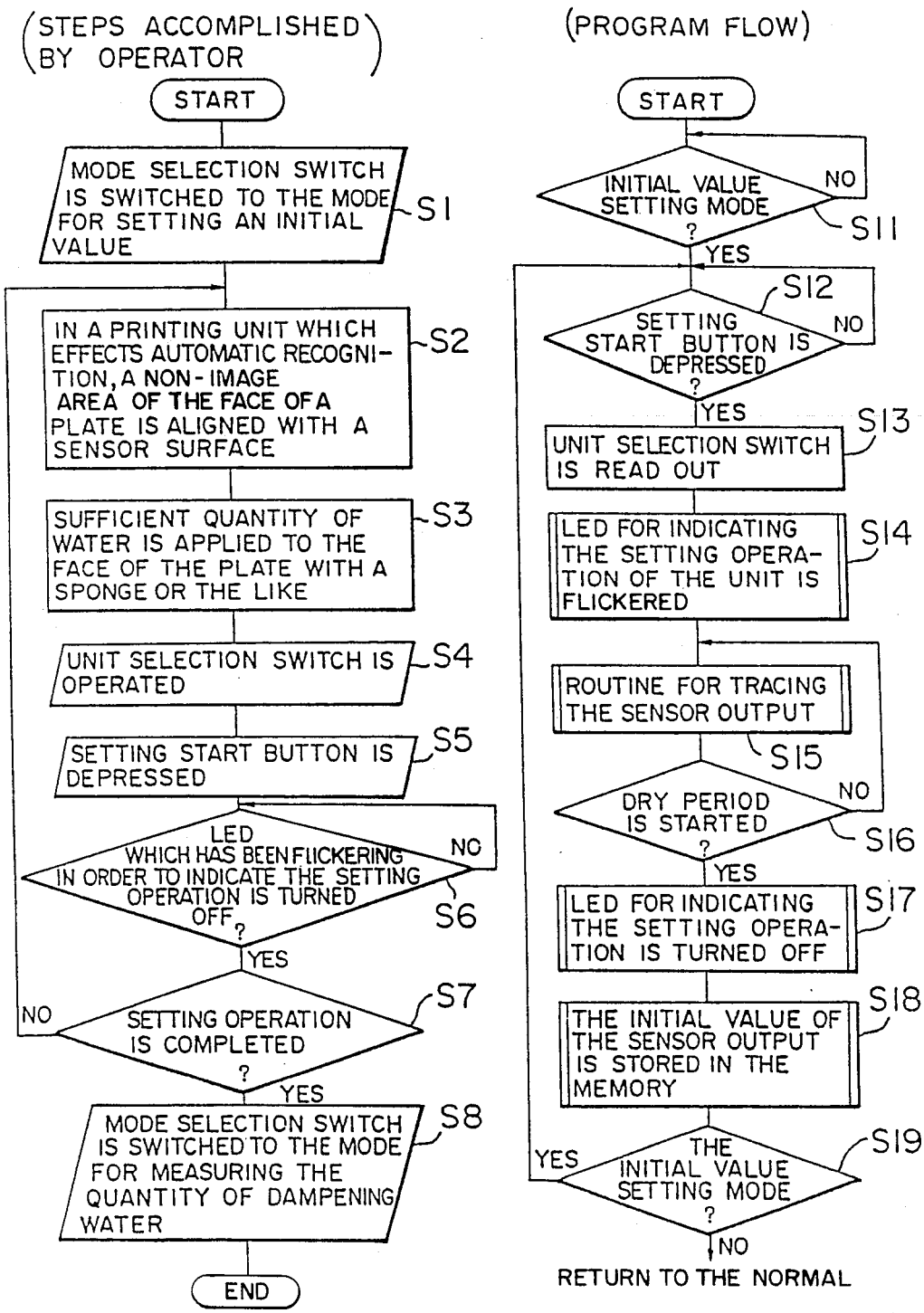
FIG. 10 is a flowchart used to explain a calibration method in accordance with the present invention.

FIG. 10 is a flowchart showing a program for setting an initial value and the steps carried out by an operator and those done by the device are shown independently of each other.

First the operator switches a mode selection 128, which can be switched between the measurement mode and the initial value setting mode, to the initial value setting mode so that CPU 122 starts the program for automatically recognizing an initial value (S1). Then the device detects the initial value setting mode and starts the step for setting an initial value (S11).

Thereafter the plate cylinder 14 is so rotated that the non-image area coincides with a sensing surface in each printing unit for which an initial value is set (S2). Next the face of a plate is sufficiently applied with water by using a sponge or the like until the face is saturated (S3) and then a unit selection switch 130 is switched to a predetermined printing unit (S4). Thereafter a setting initiating button 129 is depressed (S5).

CPU detects that the setting initiating button 129 has been depressed (S12) and reads out the predetermined number selected by the unit selection switch 130 (S13) and turns on and off or flicker an alarming LED so that the operator may know that the step for setting an initial value is being carried on (S14). Thereafter a tracing routine is immediately effected (S15). In this case the rod-shaped LED 125 displays the magnitude of a sensor signal. When the dried condition is detected as a result of tracing the sensor output to be described in more detail hereinafter (S16), the alarming LED is turned off (S17) and the initial value of the sensor which is automatically sensed is stored in a memory (S18). Thereafter CPU 122 reads out the mode set by the mode selection switch 128 (S19) and if the normal measurement mode is detected, the operation for setting an initial value is switched to the normal measurement operation.

During the initial value setting operation, the operator watches the alarming LED (S6) and after the flicker of the LED ends, the operator decides whether to repeat the operation for another printing unit (S7). If the operation is terminated, the mode selection switch 128 is switched to the normal measurement mode (S8).

Next the algorithm for tracing the sensor output will be described.

Figure 11:
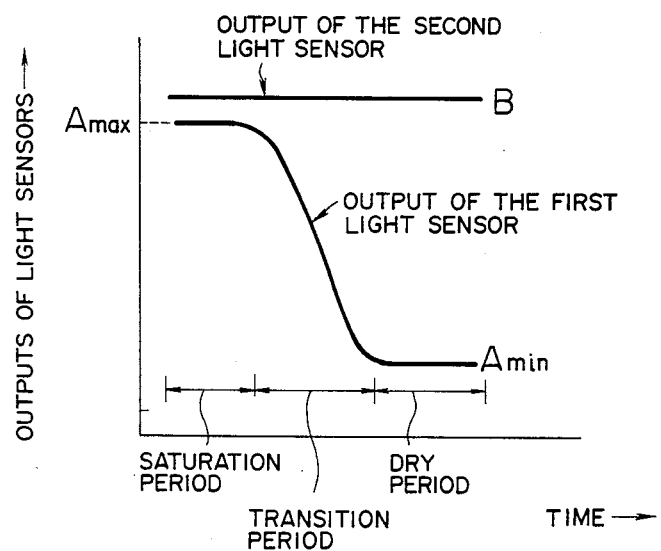
FIG. 11 is a view used to explain the underlying principle of the calibration method shown in FIG. 10.

FIG. 11 shows the output curves of the sensors from the time when the face of the plate is saturated with dampening water to the time when it has been completely dried. The output of the first light sensor shows $A_{max}$ during the saturation period and then gradually drops during the transition period and reaches a constant output $A_{min}$ during the drying period. On the other hand, the output of the second light sensor remains a constant output B regardless of the fact that the face of the plate is saturated or dried. Therefore these output curves are traced to automatically obtain the maximum output $A_{max}$, the minimum output $A_{min}$ and the average output B.

Figure 12:
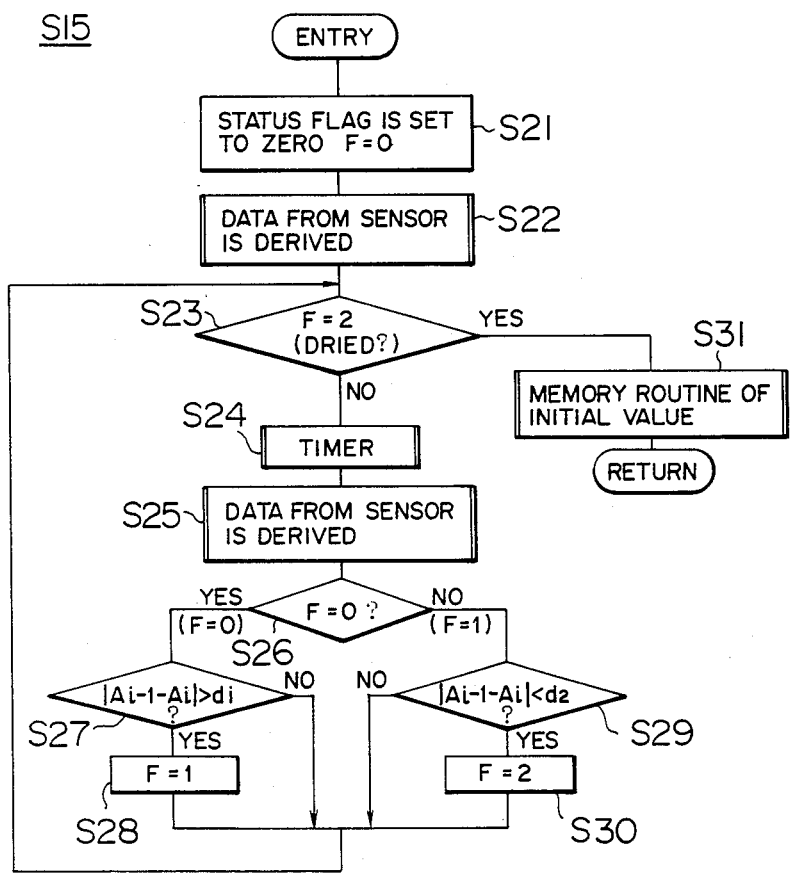
FIG. 12 is a flowchart used to explain in more detail the step (S15) shown in FIG. 10.

FIG. 12 is a flowchart used to explain such tracing algorithm which is utilized to determine the parameters $A_{SAT}$, $A_{DRY}$ and B in the equation for calibration.

Prior to the tracing, the status of flag F is made zero (S21) by depressing a setting initiating button so that of the saturation period, the transition period and the dry period, the saturation period is selected. Next the output from the sensor is stored in the memory (S22). In this case, in order to reduce the external noise to a minimum, about ten sensor data are sampled at an interval of, for instance, five milliseconds. The average of the sampled data is obtained and stored in the memory as one sampling data.

Thereafter the status of the flag F is detected (S23) and if $F \neq 2$, about a time interval of about five minutes is provided (S24) and then data is stored (S25). Thereafter it is decided whether the sensor signal is traced or not (S26–S30) in a manner described below.

When the status flag is zero; that is, when the face of the plate is still saturated until five minutes ago, the data $A_{i-1}$ from the first light sensor five seconds ago is compared with the data Ai just derived and their difference is compared with a predetermined constant value $d_1$ (S27). When the former is detected as being greater than the latter, the transition period is detected so that the flag becomes 1 again (S28) and the operation of the timer (S24) is carried out. If the flag F is 1; that is, when it is detected that the transition period existed five seconds ago, the difference between the data $A_{i-1}$ of the first light sensor five seconds ago and the data $A_i$ just derived is compared with a predetermined constant $d_2$ (S29). If the former is smaller, the dry period is detected so that the flag F becomes 2 (S30). Thereafter a routine for memorizing an initial value is carried out (S31) through the step (S23).

The memory routine (S31) obtains from the data previously stored, the maximum output value, the minimum output value of the first light sensor and the average output value of the second light sensor. Thus, obtained values $A_{max}$, $A_{min}$ and B are stored in the memory and based on this stored data, the measurement of the equantity of dampening water is calibrated in accordance with the above-described equations.

Figure 14A:
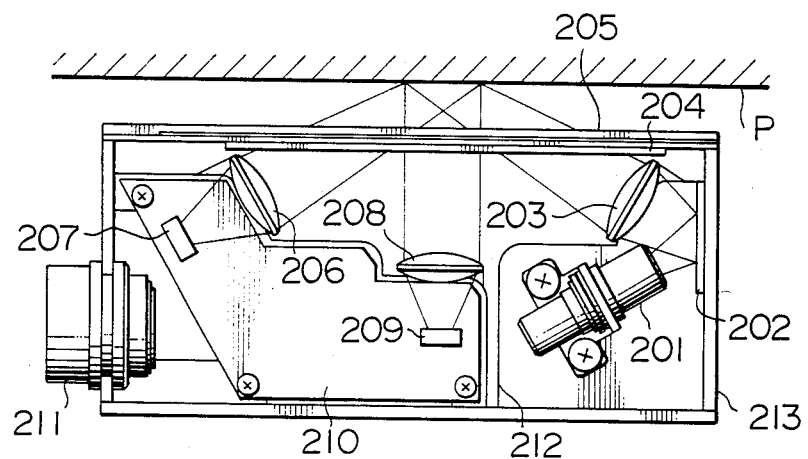
FIGS. 14(a), (b) and (c) show the construction of a device in accordance with the present invention.
Figure 14B:
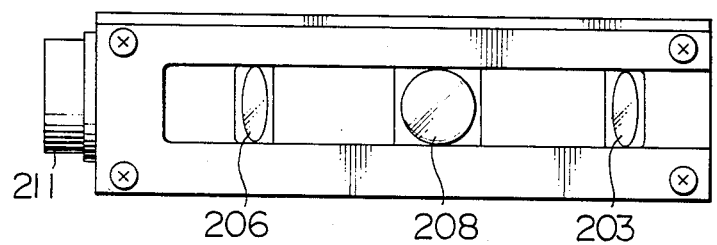
Figure 14C:
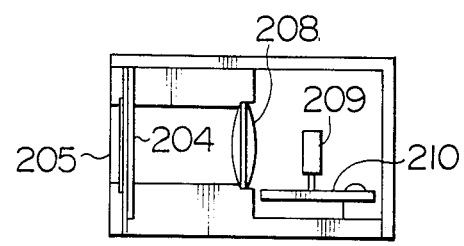

FIGS. 14(a), (b) and (c) show the mechanical construction of the device in accordance with the present invention. The light beam emitted from the light source 201 is redirected by the mirror 202 and converged by the lens 203 and is made to impinge upon the plate P at a predetermined angle of incidence through a protective glass 204 and an anti-contamination filter 205. The light beam directly reflected from the plate P passes through the film 205 and the glass 204 again and is condensed by a condenser lens 206 and is focused on the first light sensor 207. The light rays diffusereflected from the plate P passes through the film 205 and the glass 204 and is condensed by a lens 208 disposed at right angles to the plate P to be focused on the second light sensor 209. In this case it should be noted that the condensor lens 206 is disposed with respect to the plate P at an angle equal to the angle of incidence of the light beam emitted from the light source 201.

The output signal from the first light sensor which is representative of the intensity of the light beam directly reflected from the plate P and the output signal from the second light sensor 209 which is representative of the light rays diffuse-reflected from the plate P are amplified by amplifiers on a board 210 and are derived from a connector 211 as a signal representative of the quantity of water dampening the face of the plate and a signal for calibrating the quantity of dampening water. Reference numeral 211 designates a shielding plate; and 213, a case.

Meanwhile, the filter 205 is contaminated by ink mist or the like after it has been disposed at a predetermined position in the case 213. The calibration required due to the contamination of the filter 205 is made based on the output signal of the second light sensor 209 which receives the diffuse-reflected light rays. As the filter is more and more contaminated, the output signals from the first and second light sensors 207 and 209 drops so that the signal-to-noise ratio S/N drops. As a result, the accuracy of measurement of the quantity of dampening water drops. Therefore when the filter 205 is contaminated beyond a predetermined level, it must be exchanged with a new one. The operator can visually detect whether the filter 205 must be replaced or not, but according to this embodiment the following method is employed.

Figure 15:
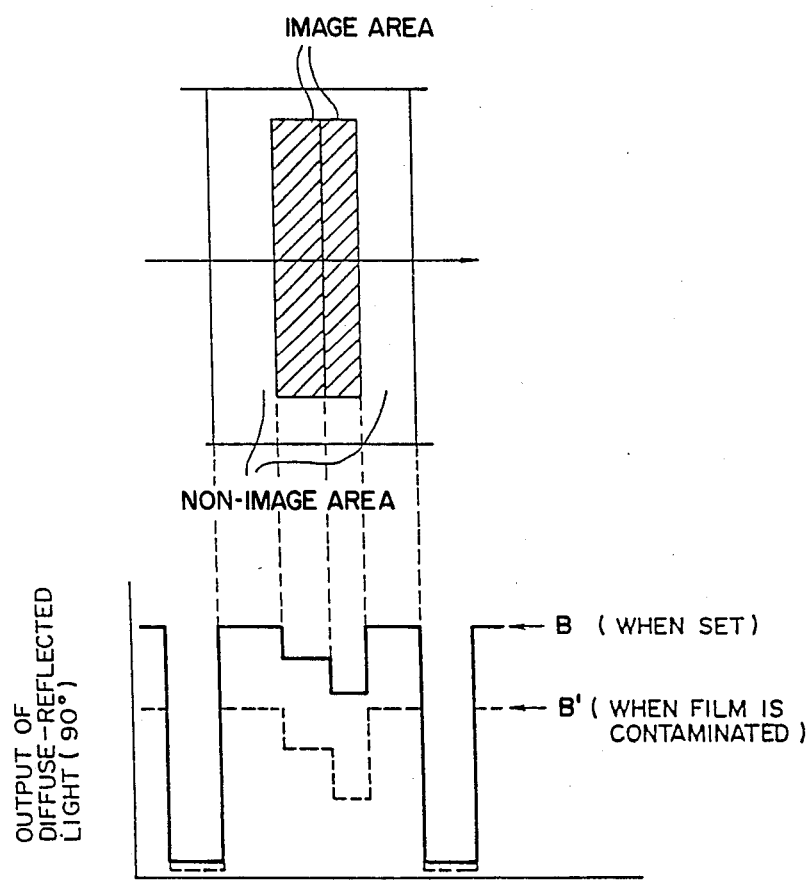
FIG. 15 shows the variations in output from a sensor when the sensor is contaminated.

That is, the device as shown in FIG. 4 is used to store the output B of the second light sensor 209, which receives the light rays diffuse-reflected at the non-image area of the plate P shown in FIG. 15, into an arithmetic unit 218. Thereafter, the ratio between the output B' from the second light sensor which receives the diffuse-reflected light rays and the value B is obtained. When the ratio thus obtained drops below a predetermined value, an alarm LED 126 disposed on the top of a display device 13 is turned on so that the operator detects that the contaminated filter must be replaced. The predetermined value is from $\frac{1}{3}$ to $\frac{1}{2}$. FIG. 15 shows the decrease in signal level due to the contamination of the film 5.

So far the method for calibrating only one sensor has been described, but it is understood that the same method may be equally used to calibrate a plurality of sensors.

In the embodiment described above, the maximum and minimum values of the first light sensor are used as the initial values, but it is to be understood that instead of the maximum value, the average value of the past data before the plate starts to dry or the same data which have been sampled predetermined times may be used. Furthermore instead of the minimum value, the average value of the data lower than a predetermined level or the same data which have been sampled predetermined times may be used. In addition, when a time interval from the period when the face of the plate is saturated with the dampening water to the period when the face of the plate is completely dried is approximately known, it is not necessary to sequentially divide into the saturation period, the transition period and the dry period. In this case, the data are stored after a predetermined interval of time and the initial values are determned according to the method described above.

What is claimed is:

1. A device for measuring the quantity of water dampening a face of an offset printing plate comprising:
   a light source for projecting a light beam at a suitable projection angle to the face of the offset printing plate;
   a first light sensor angularly disposed with respect to said face of said offset printing plate at an angle equal to said projection angle of said beam projected from said light source so as to receive the light beam directly reflected from the face of said offset printing plate;
   a second light sensor disposed substantially normal relative to the face of said offset printing plate so as to receive diffused portions of the light beam reflected from the face of said offset printing plate; and
   a display and operation means for receiving outputs from said first and second light sensors so as to compute a quantity of water dampening the face of said offset printing plate and displaying an indication of the quantity of water, said display and operation means receiving said outputs by detecting an output $A_{SAT}$ from said first light sensor when the face of said offset printing plate is essentially saturated with dampening water, detecting an output $A_{DRY}$ from said first light sensor when said face of said offset printing plate is essentially dry, detecting an output from said second light sensor and determining the quantity of dampening water according to the following equation:

$$\frac{A - A_{DRY}}{A_{SAT} - A_{DRY}} =$$

-continued
$$\frac{A' - \left(\frac{B'}{B}\right)^b A_{DRY}}{\left(\frac{B'}{B}\right)^b A_{SAT} - \left(\frac{B'}{B}\right)^b A_{DRY}}$$

wherein A is the output from the first light sensor representing the quantity of dampening water present, $A' = \alpha A$, $\alpha$ is the variation rate of the output A from the first sensor, $B' = \beta B$, $\beta$ is the variation rate of output B from the second sensor expressed as $b\sqrt{\alpha}$ and b is a constant having a value between 1.0 and 2.0.

2. The device as set forth in claim 1 further comprising means for detecting the non-image area of said face of said offset printing plate in response to the output from said second light sensor.

3. The device set forth in claim 1 further comprising means for generating a signal indicative of rotation of said offset printing plate.

4. The device set forth in claim 3, wherein said signal indicative of rotation of said offset printing plate is generated in response to detection of a clamp of said printing plate.

5. A method for measuring the quantity of water dampening the face of an offset printing plate wherein the quantity of dampening water supplied to a non-image area of the offset printing plate of an offset press is measured by utilizing a light beam reflected from the face of the offset printing plate, said method comprising:
   detecting the light beam directly reflected from the offset printing plate at an angle equal to the angle of incidence between the light beam and the offset printing plate;
   independently detecting the diffused portions of the light beam reflected in a direction normal to the face of the offset printing plate;
   detecting the non-image area of the offset printing plate in response to the diffused portions of the light beam thus detected; and
   calibrating the variations in level of said directly reflected light beam in response to the diffused portions of the light beam thus detected.

* * * * *